United States Patent [19]

Friedman

[11] Patent Number: 4,813,871
[45] Date of Patent: Mar. 21, 1989

[54] DENTAL VISCOUS MATERIAL DISPENSER

[76] Inventor: Stephen J. Friedman, 7220 Dockside La., Columbia, Md. 21045

[21] Appl. No.: 101,283

[22] Filed: Sep. 25, 1987

[51] Int. Cl.⁴ .............................................. A61C 5/04
[52] U.S. Cl. ........................................ 433/90; 222/386
[58] Field of Search ..................... 433/90, 89; 222/386

[56] References Cited

U.S. PATENT DOCUMENTS

| | | | |
|---|---|---|---|
| 2,648,906 | 8/1953 | Holmes | 433/90 |
| 2,837,824 | 6/1958 | Moller | 433/90 |
| 3,521,356 | 7/1970 | Newman | 433/89 |
| 3,581,399 | 6/1971 | Dragan | 433/90 |
| 4,295,828 | 10/1981 | Rudler | 433/90 |

Primary Examiner—John J. Wilson
Attorney, Agent, or Firm—Morton J. Rosenberg

[57] ABSTRACT

A viscous material dispenser (10) for the controlled application of a viscous dental material from a capsule (40) through an applicator tip (50) with nozzle (55). Capsule (40) is inserted within syringe barrel (30) and retained in place by capsule locking means (20). Syringe barrel (30) includes a slot (32) through which retaining spring (24) passes for contact with an end of capsule (40). Retention spring (24) follows the helical contour of slot (32), through which it passes, as capsule locking means (20) is rotated. Clockwise rotation forces capsule (40) toward applicator tip (50) and thus securing capsule (40) in place. Capsule (40) includes plunger (42) which is lockingly coupled to applicator (44) by barb (48). This arrangement permits plunger (42) to alternately apply pressure and suction to the viscous material such that a controlled volume can be aspirated through nozzle (55).

18 Claims, 2 Drawing Sheets

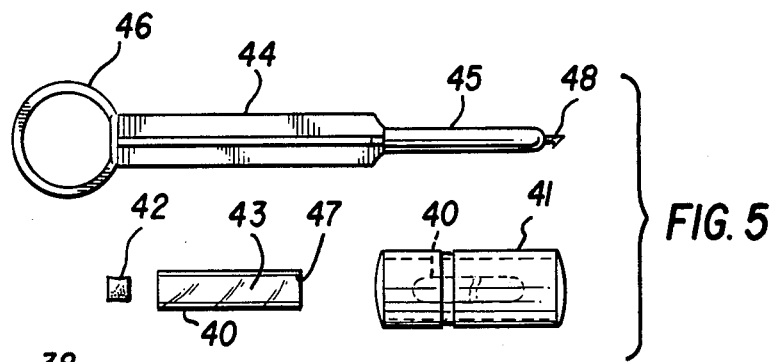
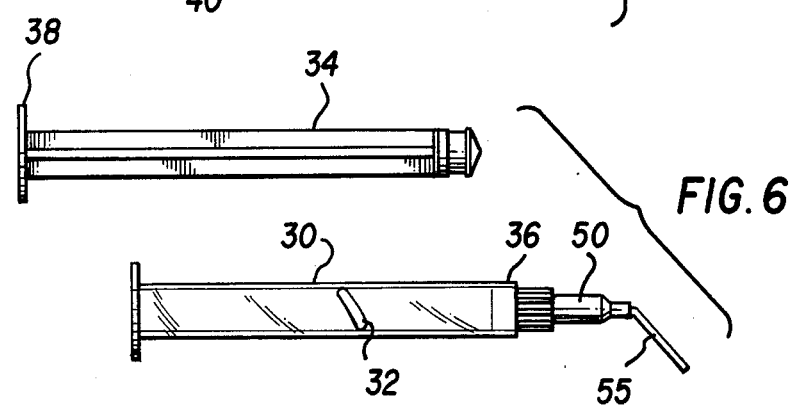
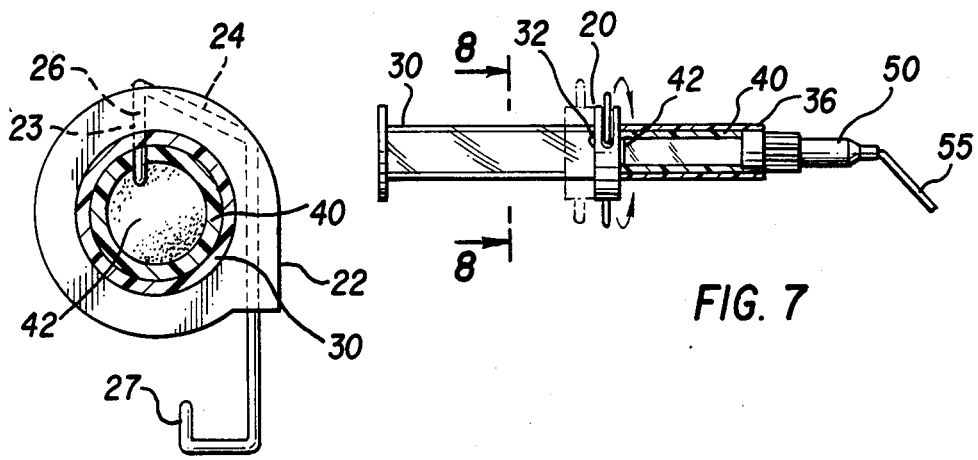

DENTAL VISCOUS MATERIAL DISPENSER

BACKGROUND OF THE INVENTION

1. Field of the Invention

This invention pertains to a dispensing system used in the dental art for the controlled application of a viscous material. In particular, this invention relates to dispensing systems having a capsule loaded with a viscous material to be aspirated. More in particular, this invention pertains to a dispensing system wherein the capsule loaded with viscous material to be aspirated is locked in position within the dispenser such that pressure or suction may be applied to the capsule and thereby to the viscous material. Still further, this invention directs itself to a viscous material dispenser having a syringe barrel on which a capsule locking means is slidingly coupled. Still further, the syringe barrel of the viscous material dispenser includes a slot having a helical contour through which a retention spring engages the end of the capsule and secures its position subsequent to rotation of the capsule locking means. Additionally, this invention directs itself to a capsule locking means having a collar slidingly coupled to the syringe barrel of the viscous material dispenser, through which the retention spring passes.

2. Prior Art

Dispensing systems for dispensing viscous dental materials are well-known in the art. The best prior art known to Applicant includes U.S. Pat. Nos. 4,619,613; 4,492,576; 4,330,280; 4,315,743; 4,198,756; 4,084,320; 3,828,434; 3,760,503; 3,618,216; 3,436,828; 3,346,147; 2,903,794; and, 683,075.

Some prior art dispensing systems such as disclosed in U.S. Pat. No. 4,084,320, dispensers for dental amalgam are disclosed which include capsules for the mixing of the amalgam components, and provide dispensers having a plunger to force the material through a nozzle. However, such systems do not provide for the convenience of dispensing the material directly from a mixing capsule, nor do they provide for a means of locking the mixing capsule within the dispenser such that both pressure and suction can be applied to the viscous material to control the volume aspirated through the dispenser nozzle.

In other types of prior art dispensing systems, such as that disclosed by U.S. Pat. Nos. 3,618,216, or 3,346,147, syringe type dental dispensers are disclosed. In these systems, a syringe having a tubular barrel is loaded with the viscous material and dispensed by application of pressure from a plunger. Such systems do not incorporate the dispensing of the viscous material directly from a cartridge or capsule into which the viscous material was prepared. Thus, no means is provided for utilizing pre-packaged materials which may be mixed within the dispensing device and immediately applied. Further, such prior art systems which might accommodate the insert of a capsule containing the viscous material to be dispensed have no means for securing the capsule within the dispenser. Without a means for securing the capsule within the dispenser, such prior art systems would be unable to create the necessary suction to halt the flow of the viscous material subsequent to the application of pressure to aspirate the material. Thus, such prior art systems are unable to provide a controlled volume of viscous material at the dispenser outlet.

SUMMARY OF THE INVENTION

A viscous material dispenser which includes a capsule for containment of the viscous material. The capsule and the viscous material contained therein are inserted into a syringe type dispenser for the controlled application of the viscous material. Additionally, there is included a locking mechanism mounted on the syringe type dispenser for securely retaining the capsule within the syringe type dispenser when a constant volume of the viscous material is being aspirated from the syringe type dispenser.

BRIEF DESCRIPTION OF THE DRAWINGS

FIG. 5 is an elevation view of the applicator, capsule, plunger, and amalgum capsule;

FIG. 6 is an elevation view of the syringe barrel and ram;

FIG. 7 is an elevation view of the dispenser of FIG. 1, partially cut-away to show the placement of the capsule; and, FIG. 8 is a sectional view of the dispenser and locking mechanism taken along the Section Lines 8—8 of FIG. 7.

DESCRIPTION OF THE PREFERRED EMBODIMENTS

Referring now to FIGS. 1-8, there is shown viscous material dispenser 10 for the controlled application of viscous dental material contained within capsule 40, subsequent to insertion within syringe barrel 30. In overall concept, the system as herein described may be generally applied to a wide variety of viscous materials. However, in particular, viscous material dispenser 10 may be applied to such viscous materials as dental cement and fillers, which require accurate placement of a controlled volume within a limited time frame.

Figure 1:
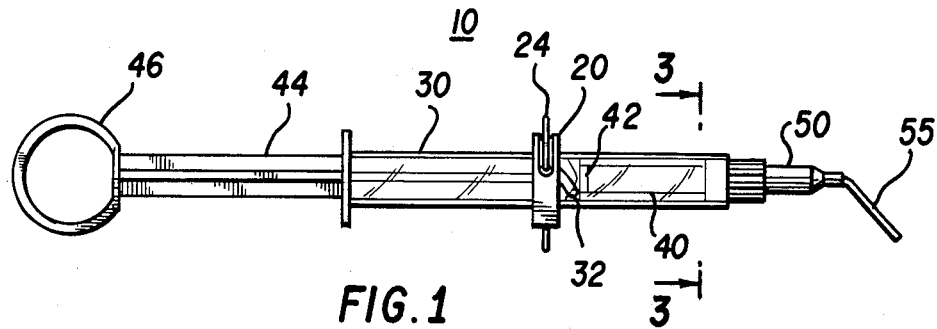
FIG. 1 is an elevation view of the viscous material dispenser.

As shown in FIG. 1, viscous material dispenser 10 includes syringe barrel 30 into which capsule 40, containing the viscous material, is inserted. Viscous material capsule 40 includes a resilient plunger 42 which fits tightly within capsule 40 for applying pressure to the viscous material responsive to force applied on applicator 44. As will be described in following paragraphs, applicator 44 is coupled to resilient plunger 42 such that both pressure and suction may be applied alternately to the viscous material to control the volume dispensed therefrom.

Important to the inventive concept of viscous material dispenser 10 is capsule locking means 20 which securely retains capsule 40 within syringe barrel 30 and thus permits resilient plunger 42 to be displaced bidirectionally, relative to capsule 40, in response to the axial displacement of applicator 44. Capsule locking means 20, shown in detail in FIG. 2, includes retention spring 24 which passes through slot 32 in syringe barrel 30 for engagement with the end of capsule 40.

Figure 4:
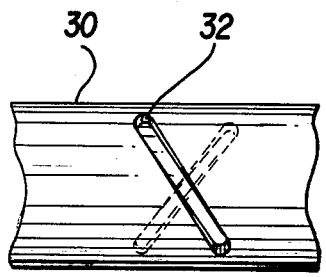
FIG. 4 is an elevation view of a portion of the dispenser shown in FIG. 1.

As shown in FIG. 4, slot 32 formed in syringe barrel 30 is offset such that it forms a helical segment through which retention spring 24 passes. As shown, slot 32 may be formed on opposing sides of syringe body 30 to provide convenient alternate positions of capsule locking means 20 relative to syringe barrel 30.

Referring back to FIG. 1, viscous material dispenser 10 further includes applicator tip 50 having angled nozzle 55 for the accurate placement of the aspirated viscous material. To accurately control the pressure and/or suction created by resilient plunger 42, applicator 44 includes thumb ring 46. Thumb ring 46 allows the user to easily pull back applicator 44 following the application of pressure, in order to create suction and thus prevent the continued flow of the viscous material from nozzle 55.

Figure 2:
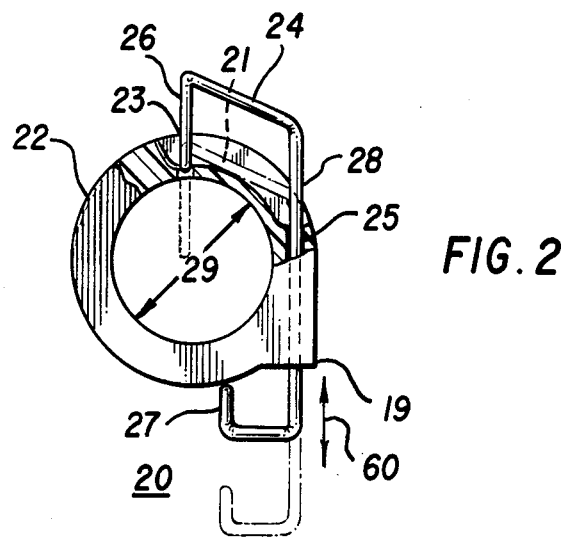
FIG. 2 is an elevation view of the capsule locking mechanism partially cut-away.

Referring now to FIG. 2, there is shown in detail, capsule locking means 20. Capsule locking means 20 includes collar 22 having a substantially cylindrical wall providing a toroidal cross-section. The cylindrical wall of collar 22 has an inside diameter 29 which is slightly larger than the outside diameter of syringe barrel 30. Such permits capsule locking means 20 to be linearly displaceable and rotatable about the external surface of syringe barrel 30. However, sufficient friction exists between collar 22 and syringe barrel 30 to maintain the position of capsule locking means 20, subsequent to the locking procedure to be described in following paragraphs.

Collar 22 of capsule locking means 20 includes a pair of holes 23 and 25 through which portions of retention spring 24 pass. Retention spring 24 is bent to form an engagement portion 26, a shaft portion 28 and a travel stop end 27. Engagement end 26 of retention spring 24 passes through hole 23 for contact with the end of capsule 40, through slot 32 in syringe barrel 30. Hole 23 passes from the external surface of collar 22 through the cylindrical wall into the interior space defined by the toroidal cross-section of collar 22.

Hole 25 passes through the cylindrical wall from one external surface of collar 22 to another, on an opposing side of collar 22 without passing through the interior space defined by the toroidal cross-section. Thus, holes 23 and 25 pass through the cylindrical wall of collar 22 in a direction which is perpendicular to the axis of the cylindrical section.

Shaft portion 28 is a segment of retention spring 24 which is parallel to engagement portion 26, but displaced from it by a spring segment of a predetermined length equal to the distance between holes 23 and 25. Shaft portion 28 passes through hole 25, whose diameter has been predetermined to permit shaft portion 28 to freely slide vertically as indicated by direction arrow 60. Retention spring 24 may therefore be moved downward allowing engagement portion 26 to pass through hole 23 and slot 32 of syringe barrel 30 to contact the end of capsule 40. Engagement portion 26 of retention spring 24 is of a predetermined length such that the end of capsule 40 can be engaged without interfering with the movement of applicator 44 and resilient plunger 42. In the alternative, retention spring 24 may be disengaged from capsule 40 and syringe barrel 30 by upward displacement of retention spring 24. This is accomplished by sliding shaft portion 28 vertically upward through hole 25. As a means of limiting the upward movement of retention spring 24, retention spring 24 includes travel stop end 27 which is hook-shaped for contact with the external surface of collar 22 when the maximum displacement of shaft portion 28 through hole 25 is reached. This limitation on the displacement of retention spring 24 prevents retention spring 24 from being separated from collar 22, and subsequently misplaced.

While not important to the inventive concept, collar 22 may include a channel 21 formed in the surface of the cylindrical wall of collar 22, between holes 23 and 25. Channel 21 provides a recess for receipt of the portion of retention spring 24 between engagement portion 26 and shaft portion 28. Collar 22 may also include an increased wall thickness 19 in the area of hole 25 to provide the necessary mechanical strength for collar 22 in the area surrounding hole 25.

Figure 3:
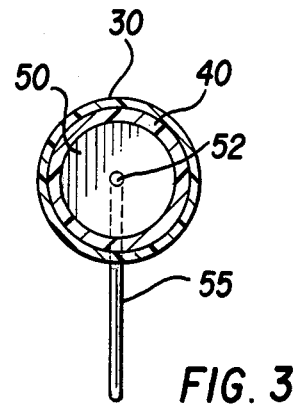
FIG. 3 is a sectional view of the distal end of the dispenser taken along the Section Lines 3—3 of FIG. 1.

Referring now to FIG. 3, there is shown a sectional view of the distal end of syringe barrel 30. As shown, capsule 40 is concentrically located within syringe barrel 30 adjacent the applicator tip 50. A passage 52 is provided from applicator tip 50 through nozzle 55 through which the viscous material contained within capsule 40 may be aspirated or withdrawn by force applied to resilient plunger 42 in cooperation with applicator 44.

Referring now to FIG. 5, there is shown applicator 44, plunger 42, capsule 40, and amalgum capsule 41. As shown, capsule 40 is a longitudinally directed cylindrical tube defining an interior cavity 43. The viscous material which is to be applied with dispenser 10 is placed within the cavity 43 of capsule 40. The viscous material dispensed in the embodiment herein described is a glass ionomer adhesive commonly used in the dental art. Adhesives of this type are prepared by mixing two or more components just prior to their application. The components may be mixed externally to form the viscous adhesive compound and then subsequently loaded into capsule 40. As a particular advantage of the inventive concept described herein, the required components of the desired viscous material may be added to capsule 40 in combination with amalgum capsule 41, which is a standard mixing container utilized in the dental art. Thus, the components of the adhesive system are added to capsule 40 subsequent to capsule 40 being inserted in one portion of amalgum capsule 41. Amalgum capsule 41 may then be sealed for mixing in a triturator as is commonly done for dental filling material. Plunger 42 may be inserted or sealed in one end of capsule 40 prior to insertion into amalgum capsule 41 for titration. Alternatively, after mixing, capsule 40 may be removed from amalgum capsule 41 and is then sealed at one end by plunger 42 which is inserted into cavity 43. Capsule 40 may then be inserted into syringe barrel 30 as will be further described in following paragraphs. Such provides a convenient method of preparing and dispensing fast setting materials, without the need to consume valuable time transferring the prepared material from a mixing container to the dispenser, a portion at a time.

Although the addition of the viscous material to capsule 40 has been described in detail for the embodiment disclosed, such should not preclude the use of a capsule 40 containing the individual components of the viscous material separated by one or more rupturable membranes and having plunger 42 pre-installed. Such a pre-packaged system is envisioned by this inventor to provide a convenient means for preparing a fast setting adhesive or filler material and subsequently rapidly applying the compound from dispenser 10.

Referring now to FIG. 6, there is shown syringe barrel 30 and ram 34. As previously described, capsule 40 containing the viscous material to be dispensed by system 10 and resilient plunger 42, is inserted into the syringe barrel 30. Capsule 40 is then positioned to the distal end 36 of syringe barrel 30 by insertion of ram 34 into syringe barrel 30. Pressure applied to ram 34 at the flattened end 38, forces capsule 40 forward such that open end 47 of capsule 40, shown in FIG. 5, is adjacent applicator tip 50. Applicator tip 50 with nozzle 55 is releasably secured to syringe barrel 30 by methods standard in the art for hypodermic syringe devices. It is to be understood that nozzle 55 may include nozzles of varying internal through passage diameters dependent on the usage. Additionally, nozzle 55 may include a tapered opening through passage to permit cutting of nozzle 55 to provide a predetermined through passage diameter.

Subsequent to capsule 40 being positioned within syringe barrel 30 by ram 34, ram 34 is removed and applicator 44 is inserted into syringe barrel 30 to displace resilient plunger 42 and thereby apply pressure to the viscous material contained within capsule 40.

Referring back to FIG. 5, there is shown applicator 44 having thumb ring 46 at its proximal end. On the opposing end, applicator 44 includes barb 48 for coupling applicator 44 to resilient plunger 42. Barb 48 is able to penetrate resilient plunger 42 and remain coupled thereto as applicator 44 is withdrawn to create a negative pressure within capsule 40 which is transferred to applicator tip 50 and nozzle 55, as they are fluidly coupled. The distal end 45 of applicator 44, to which barb 48 is attached, is reduced in diameter such that distal end 45 is able to pass through capsule 40 as resilient plunger 42 is displaced axially toward end 47 of capsule 40.

Referring now to FIGS. 7 and 8, there is shown the method by which capsule 40 is retained within syringe barrel 30 by locking means 20. Capsule 40 is shown in position subsequent to use of ram 34, as has been previously described. Ram 34 may be a conventional syringe plunger well-known in the art, and not important to the inventive concept herein described. Capsule locking means 20 with retention spring 24 in the elevated position shown in FIG. 2 may be slipped over syringe barrel 30 and positioned adjacent helical slot 32 formed in syringe barrel 30.

As shown in FIG. 8, retention spring 24 when displaced downwardly positions the engagement portion 26 through hole 23. Engagement portion 26 of retention spring 24 passes through slot 32 and just past the cylindrical wall of capsule 40. Thus, this allows engagement portion 26 of retention spring 24 to contact the edge of capsule 40 without interfering with the movement through capsule 40 by distal end 45 of applicator 44.

With the capsule locking means 20 having contacted the edge of capsule 40 with engagement portion 26 of retaining spring 24, as shown in FIGS. 7 and 8, capsule 40 may now be secured in position. By rotation of collar 22, capsule 40 is forced against distal end 36 of syringe barrel 30 providing the fluid coupling between capsule 40 and applicator tip 50 and nozzle 55. Thus, by rotating capsule locking means 20 clockwise about syringe barrel 30, engagement portion 26 of retention spring 24 forces capsule 40 toward distal end 36 of syringe barrel 30 as engagement portion 26 follows the helical path provided by slot 32. A sidewall of slot 32 may be serrated to enhance frictional engagement of portion 26 in a constrained manner. Thus, there is provided a unique method of releasably securing a capsule containing a viscous material for controlled aspiration from a syringe type dispenser. Capsule locking means 20 provides a unique method of securing capsule 40 within syringe barrel 30 such that resilient plunger 42 may be displaced bi-directionally within capsule 40 to create both positive and negative pressures, alternately, for the aspiration of controlled volumes of viscous material.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features maybe used independently of other features, and in certain cases, particular locations of elements may be reversed or interposed, all without departing from the spirit or scope of the invention as defined in the appended claims.

What is claimed is:

1. A viscous material dispenser for the controlled application of a viscous material, comprising:
    (a) capsule means for containment of said viscous material;
    (b) dispensing means for said controlled application of said viscous material from said capsule means, said capsule means being insertable into said dispensing means; and,
    (c) locking means mounted on said dispensing means for securely retaining said capsule means within said dispensing means when a controlled volume of said viscous material is being aspirated from said dispenser means, said locking means being slidably displaceable on said dispensing means, said locking means extending internal said dispensing means and having a toroidal collar including a substantially cylindrical wall member and a retention spring member slidingly coupled to said toroidal collar.

2. The viscous material dispenser as recited in claim 1 where said capsule means includes a hollow cylindrical tube having a first and second end.

3. The viscous material dispenser as recited in claim 2 where said capsule means further includes a resilient plunger member for insert into said first end of said hollow cylindrical tube.

4. The viscous material dispenser as recited in claim 3 where said capsule means further includes an applicator member having a first end adapted for locking engagement with said resilient plunger member and thereby exerting force against said viscous material, said applicator member being insertable and slidingly coupled to said dispensing means.

5. The viscous material dispenser as recited in claim 4 where said dispensing means includes a housing member having a longitudinally directed cylindrical wall forming a cylindrical cavity for insert of said capsule means.

6. The viscous material dispenser as recited in claim 5 where said locking means is slidingly mounted on an exterior surface of said cylindrical wall of said housing member, said locking means passing internal said cavity through a slot formed through said cylindrical wall of said housing means.

7. The viscous material dispenser as recited in claim 6 where said toroidal collar substantially cylindrical wall member has a predetermined inside diameter defining an interior opening.

8. The viscous material dispenser as recited in claim 7 where said retention spring member has a shaft portion and an engagement portion.

9. The viscous material dispenser as recited in claim 8 where said substantially cylindrical wall member of said toroidal collar has a first and second hole formed therein, said first and second hole being directed through said substantially cylindrical wall member of said toroidal collar substantially perpendicular to the axis of said substantially cylindrical wall member, said first hole passing from the exterior surface of said wall member to said interior opening, said second hole passing through said exterior surface of said wall member on a first side of said collar to said exterior surface on an opposing side of said collar without passing through said interior opening.

10. The viscous material dispenser as recited in claim 9 where said engagement portion of said retention spring member reversibly passes through said first hole in said toroidal collar and said slot in said housing member for contacting said first end of said hollow cylindrical tube subsequent to said hollow cylindrical tube being inserted into said housing member.

11. The viscous material dispenser as recited in claim 10 where said shaft portion of said retention spring member passes through said second hole in said toroidal collar to slidingly couple said retention spring to said toroidal collar.

12. The viscous material dispenser as recited in claim 11 where said slot formed in said housing member has a helical contour.

13. The viscous material dispenser as recited in claim 12 where said toroidal collar is rotatably displaceable subsequent to said engagement portion of said retention spring member contacting said first end of said hollow cylindrical tube for locking said cylindrical tube in position against one end of said housing member.

14. A retention system for securing a cartridge, containing a viscous material within a dispenser, comprising:
(a) a cylindrical dispenser housing member being longitudinally directed and having a first and a second end to form a cavity for insert of said cartridge through said first end, said dispenser housing member having at least one helical slot between said first and second ends formed therein, said second end of said dispenser housing member being substantially closed to prevent said cartridge from passing therethrough, said second end of said dispenser housing member including an opening of predetermined size for passage of said viscous material from said cartridge through said dispenser housing member; and,
(b) locking means slidingly coupled to said dispenser housing member for contiguously contacting an end of said cartridge through said helical slot formed in said dispenser housing subsequent to said cartridge being inserted into said dispenser housing member, said locking means including a toroidal collar having a substantially cylindrical wall member, said substantially cylindrical wall member having a predetermined internal diameter defining an interior opening and further including a retention spring member slidingly coupled to said toroidal collar, said retention spring member having a shaft portion and an engagement portion.

15. The retention spring as recited in claim 14 where said substantially cylindrical wall member of said toroidal collar has a first and second hole formed therein, said first and second hole being directed through said substantially cylindrical wall member of said toroidal collar substantially perpendicular to the axis of said substantially cylindrical wall member, said first hole passing from the exterior surface of said wall member to said interior opening, said second hole passing through said exterior surface of said wall member on a first side of said collar to said exterior surface on an opposing side of said collar without passing through said interior opening.

16. The retention system as recited in claim 15 where said engagement portion of said retention spring member reversibly passes through said first hole in said toroidal collar and said helical slot in said dispenser housing member for contacting said end of said cartridge subsequent to said cartridge being inserted into said dispenser housing member.

17. The retention system as recited in claim 16 where said shaft portion of said retention spring member passes through said second hole in said toroidal collar to slidingly couple said retention spring to said toroidal collar.

18. The retention system as recited in claim 17 where said toroidal collar is rotatably displaceable subsequent to said engagement portion of said retention spring member contacting said end of said cartridge for locking said cartridge in position against said second end of said dispenser housing member.

* * * * *